(12) United States Patent  (10) Patent No.: US 8,391,985 B2
McDonald  (45) Date of Patent: Mar. 5, 2013

(54) ELECTRODE ARRAY HAVING CONCENTRIC WINDOWED CYLINDER ELECTRODES AND METHODS OF MAKING THE SAME

(75) Inventor: Matthew Lee McDonald, Pasadena, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 164 days.

(21) Appl. No.: 12/945,623

(22) Filed: Nov. 12, 2010

(65) Prior Publication Data

US 2011/0130803 A1 Jun. 2, 2011

Related U.S. Application Data

(60) Provisional application No. 61/265,229, filed on Nov. 30, 2009.

(51) Int. Cl.
*A61N 1/00* (2006.01)
(52) U.S. Cl. .................................................. 607/45
(58) Field of Classification Search .................. 607/45
See application file for complete search history.

(56) References Cited

U.S. PATENT DOCUMENTS

| | | | |
|---|---|---|---|
| 4,112,953 A | 9/1978 | Shanker et al. | |
| 4,350,159 A | 9/1982 | Gouda | |
| 4,471,777 A | 9/1984 | McCorkle, Jr. | |
| 4,565,200 A | 1/1986 | Cosman | |
| 4,577,643 A | 3/1986 | Beranek | |
| 4,602,624 A | 7/1986 | Naples et al. | |
| 4,630,611 A | 12/1986 | King | |
| 4,668,221 A | 5/1987 | Luther | |
| 4,744,370 A | 5/1988 | Harris | |
| 4,886,065 A | 12/1989 | Collins, Jr. | |
| 4,931,056 A | 6/1990 | Ghajar et al. | |
| 4,955,891 A | 9/1990 | Carol et al. | |
| 5,000,194 A | 3/1991 | van den Honert et al. | |
| 5,006,122 A | 4/1991 | Wyatt et al. | |
| 5,114,424 A | 5/1992 | Hagan et al. | |

(Continued)

FOREIGN PATENT DOCUMENTS

| | | |
|---|---|---|
| EP | 0580928 A1 | 2/1994 |
| EP | 0650694 B1 | 7/1998 |

(Continued)

OTHER PUBLICATIONS

"System and Method for Selective Multi-site Microelectrode Recording," IP.com, IPCOM000016587D, Jul. 1, 2003.

(Continued)

*Primary Examiner* — George Manuel
*Assistant Examiner* — Robert N Wieland
(74) *Attorney, Agent, or Firm* — Frommer Lawrence & Haug LLP; Bruce E. Black

(57) ABSTRACT

A device for brain stimulation includes a lead body having a distal end section and at least one inner conductive cylinder with at least one inner window cut out from the inner cylinder. The inner cylinder is disposed at the distal end section of the lead body. The device also includes an outer conductive cylinder with at least one outer window cut out from the outer cylinder. The outer cylinder is secured to and disposed concentric to the inner cylinder with a portion of each of the at least one inner cylinder aligned with the at least one outer window of the outer cylinder. The device further includes an insulator configured and arranged to electrically insulate each of the at least one inner cylinder and the outer cylinder.

20 Claims, 12 Drawing Sheets

U.S. PATENT DOCUMENTS

| | | |
|---|---|---|
| 5,116,345 A | 5/1992 | Jewell et al. |
| 5,135,001 A | 8/1992 | Sinofsky et al. |
| 5,300,080 A | 4/1994 | Clayman et al. |
| 5,303,704 A | 4/1994 | Molacek |
| 5,318,041 A | 6/1994 | DuBois et al. |
| 5,330,485 A | 7/1994 | Clayman et al. |
| 5,374,285 A | 12/1994 | Vaiani et al. |
| 5,411,025 A | 5/1995 | Webster, Jr. |
| 5,450,846 A | 9/1995 | Goldreyer |
| 5,458,629 A | 10/1995 | Baudino et al. |
| 5,522,874 A | 6/1996 | Gates |
| 5,618,287 A | 4/1997 | Fogarty et al. |
| 5,628,313 A | 5/1997 | Webster, Jr. |
| 5,711,316 A | 1/1998 | Elsberry et al. |
| 5,713,922 A | 2/1998 | King |
| 5,728,148 A | 3/1998 | Bostrom et al. |
| 5,752,937 A | 5/1998 | Otten et al. |
| 5,782,239 A | 7/1998 | Webster, Jr. |
| 5,800,350 A | 9/1998 | Coppleson et al. |
| 5,843,148 A | 12/1998 | Gijsbers et al. |
| 5,913,882 A | 6/1999 | King |
| 5,925,073 A | 7/1999 | Chastain et al. |
| 5,938,688 A | 8/1999 | Schiff |
| 5,978,713 A | 11/1999 | Prutchi et al. |
| 5,987,361 A | 11/1999 | Mortimer |
| 6,011,996 A | 1/2000 | Gielen et al. |
| 6,018,684 A | 1/2000 | Bartig et al. |
| 6,026,567 A | 2/2000 | Swoyer et al. |
| 6,066,165 A | 5/2000 | Racz |
| 6,134,478 A | 10/2000 | Spehr |
| 6,161,047 A | 12/2000 | King et al. |
| 6,167,311 A | 12/2000 | Rezai |
| 6,181,971 B1 | 1/2001 | Doan |
| 6,261,300 B1 | 7/2001 | Carol et al. |
| 6,301,492 B1 | 10/2001 | Zonensheyn |
| 6,343,226 B1 | 1/2002 | Sunde et al. |
| 6,413,263 B1 | 7/2002 | Lobdill et al. |
| 6,416,520 B1 | 7/2002 | Kynast et al. |
| 6,456,869 B1 | 9/2002 | Raylman et al. |
| 6,456,889 B2 | 9/2002 | Pianca et al. |
| 6,510,347 B2 | 1/2003 | Borkan |
| 6,529,774 B1 | 3/2003 | Greene |
| 6,556,873 B1 | 4/2003 | Smits |
| 6,564,078 B1 | 5/2003 | Marino et al. |
| 6,572,624 B2 | 6/2003 | U et al. |
| 6,575,968 B1 | 6/2003 | Eggers et al. |
| 6,597,954 B1 | 7/2003 | Pless et al. |
| 6,687,549 B1 | 2/2004 | Helland et al. |
| 6,757,970 B1 | 7/2004 | Kuzma et al. |
| 6,782,292 B2 | 8/2004 | Whitehurst |
| 6,849,062 B2 | 2/2005 | Kantor |
| 7,027,852 B2 | 4/2006 | Helland |
| 7,033,326 B1 | 4/2006 | Pianca et al. |
| 7,047,084 B2 | 5/2006 | Erickson et al. |
| 7,174,219 B2 | 2/2007 | Wahlstrand et al. |
| 7,177,701 B1 | 2/2007 | Pianca |
| 7,177,702 B2 | 2/2007 | Wallace et al. |
| 7,212,867 B2 | 5/2007 | Van Venrooij et al. |
| 7,292,890 B2 | 11/2007 | Whitehurst et al. |
| 7,668,601 B2 | 2/2010 | Hegland et al. |
| 7,840,188 B2 | 11/2010 | Kurokawa |
| 7,860,570 B2 | 12/2010 | Whitehurst et al. |
| 8,041,309 B2 | 10/2011 | Kurokawa |
| 2001/0027336 A1 | 10/2001 | Gielen et al. |
| 2002/0151924 A1 | 10/2002 | Shiber |
| 2002/0156513 A1 | 10/2002 | Borkan |
| 2002/0183817 A1* | 12/2002 | Van Venrooij et al. ....... 607/116 |
| 2003/0212446 A1 | 11/2003 | Kaplan et al. |
| 2004/0059392 A1 | 3/2004 | Parramon et al. |
| 2004/0122499 A1 | 6/2004 | Westlund |
| 2004/0199235 A1 | 10/2004 | Younis |
| 2005/0004637 A1 | 1/2005 | Singhal et al. |
| 2005/0015130 A1 | 1/2005 | Gill |
| 2005/0038489 A1 | 2/2005 | Grill |
| 2005/0070983 A1 | 3/2005 | Rugnetta et al. |
| 2005/0203600 A1 | 9/2005 | Wallace et al. |
| 2005/0203602 A1 | 9/2005 | Wallace et al. |
| 2005/0222647 A1 | 10/2005 | Wahlstrand et al. |
| 2006/0025841 A1 | 2/2006 | McIntyre |
| 2006/0095088 A1 | 5/2006 | De Ridder |
| 2006/0100671 A1 | 5/2006 | De Ridder |
| 2006/0116742 A1 | 6/2006 | De Ridder |
| 2006/0149335 A1 | 7/2006 | Meadows |
| 2006/0149336 A1 | 7/2006 | Meadows |
| 2006/0168805 A1 | 8/2006 | Heglund et al. |
| 2006/0173262 A1 | 8/2006 | Heglund et al. |
| 2006/0247697 A1 | 11/2006 | Sharma et al. |
| 2006/0259110 A1 | 11/2006 | Wallace et al. |
| 2007/0150034 A1 | 6/2007 | Rooney et al. |
| 2007/0203540 A1 | 8/2007 | Goetz et al. |
| 2007/0203542 A1 | 8/2007 | Goetz et al. |
| 2007/0203543 A1 | 8/2007 | Stone et al. |
| 2007/0203546 A1 | 8/2007 | Stone et al. |
| 2007/0213795 A1 | 9/2007 | Bradley et al. |
| 2008/0103572 A1 | 5/2008 | Gerber |
| 2008/0114230 A1 | 5/2008 | Addis |
| 2008/0147158 A1 | 6/2008 | Zweber et al. |
| 2008/0243218 A1 | 10/2008 | Bottomley et al. |
| 2009/0204193 A1 | 8/2009 | Kokones et al. |
| 2010/0076535 A1 | 3/2010 | Pianca et al. |
| 2010/0268298 A1 | 10/2010 | Moffitt et al. |
| 2011/0004267 A1 | 1/2011 | Meadows |
| 2011/0005069 A1 | 1/2011 | Pianca |
| 2011/0056076 A1 | 3/2011 | Hegland et al. |
| 2011/0078900 A1 | 4/2011 | Pianca et al. |
| 2011/0130816 A1 | 6/2011 | Howard et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |

FOREIGN PATENT DOCUMENTS

| | | |
|---|---|---|
| EP | 1062973 A1 | 12/2000 |
| EP | 0879016 B1 | 10/2003 |
| EP | 0832667 B1 | 2/2004 |
| EP | 1181947 B1 | 1/2006 |
| EP | 1935448 | 6/2008 |
| EP | 2092952 A1 | 8/2009 |
| WO | 9732628 A1 | 9/1997 |
| WO | 9936122 A1 | 7/1999 |
| WO | 9955411 A3 | 2/2000 |
| WO | 0038574 A1 | 7/2000 |
| WO | 02068042 A1 | 9/2002 |
| WO | 2004002288 A2 | 1/2004 |
| WO | 2004045707 A1 | 6/2004 |
| WO | 2005092432 A1 | 10/2005 |
| WO | 2006047265 | 5/2006 |
| WO | 2006083881 A1 | 8/2006 |
| WO | 2006083884 A1 | 8/2006 |
| WO | 2005102446 A1 | 11/2006 |
| WO | 2006133445 A2 | 12/2006 |
| WO | 2007097860 A1 | 8/2007 |
| WO | 2007097873 A1 | 8/2007 |
| WO | 2007100427 A1 | 9/2007 |
| WO | 2007100428 A1 | 9/2007 |
| WO | 2008053789 A1 | 5/2008 |
| WO | 2008115426 A1 | 9/2008 |
| WO | 2009025816 A1 | 2/2009 |

OTHER PUBLICATIONS

"Universal Instrument Guide and Surgical Insertion Tool for Stereotactic Frames," IP.com, IPCOM000011023D, Feb. 7, 2003.

International Search Report and Written Opinion for International Patent Application No. PCT/US2009/057953, mailed Apr. 21, 2010.

U.S. Appl. No. 13/275,112, filed Oct. 17, 2011.

U.S. Appl. No. 13/363,059, filed Jan. 31, 2012.

U.S. Appl. No. 13/368,982, filed Feb. 8, 2012.

U.S. Appl. No. 13/369,013, filed Feb. 8, 2012.

U.S. Appl. No. 13/368,733, filed Feb. 8, 2012.

* cited by examiner

ELECTRODE ARRAY HAVING CONCENTRIC WINDOWED CYLINDER ELECTRODES AND METHODS OF MAKING THE SAME

CROSS-REFERENCE TO RELATED APPLICATIONS

This application claims the benefit under 35 U.S.C. §119 (e) of U.S. Provisional Patent Application Ser. No. 61/265,229 filed on Nov. 30, 2009, which is incorporated herein by reference.

FIELD

The invention is directed to devices and methods for brain stimulation including deep brain stimulation. In addition, the invention is directed to devices and method for brain stimulation using a lead having concentric windowed cylinder electrodes.

BACKGROUND

Deep brain stimulation can be useful for treating a variety of conditions including, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging (MRI) or computerized tomography (CT) scans can provide a starting point for determining where the stimulating electrode should be positioned to provide the desired stimulus to the target neurons.

Upon insertion, current is introduced along the length of the lead to stimulate target neurons in the brain. This stimulation is provided by electrodes, typically in the form of rings, disposed on the lead. The current projects from each electrode similarly and in all directions at any given length along the axis of the lead. Because of the shape of the electrodes, radial selectivity of the current is minimal. This results in the unwanted stimulation of neighboring neural tissue, undesired side effects and an increased duration of time for the proper therapeutic effect to be obtained.

In the field of deep brain stimulation, radially segmented electrode arrays (RSEA) have been developed to provide superior radial selectivity of current. Radially segmented electrode arrays are useful for deep brain stimulation because the target structures in the deep brain are often not symmetric about the axis of the distal electrode array. In some cases, a target may be located on one side of a plane running through the axis of the lead. In other cases, a target may be located at a plane that is offset at some angle from the axis of the lead. Thus, radially segmented electrode arrays may be useful for selectively simulating tissue. These radially segmented arrays may be made using concentric windowed cylinder electrodes.

BRIEF SUMMARY

In some embodiments, a device for brain stimulation includes a lead body having a distal end section and at least one inner conductive cylinder with at least one inner window cut out from the inner cylinder. The inner cylinder is disposed at the distal end section of the lead body. The device also includes an outer conductive cylinder with at least one outer window cut out from the outer cylinder. The outer cylinder is secured to and disposed concentric to the inner cylinder with a portion of each of the at least one inner cylinder aligned with the at least one outer window of the outer cylinder. The device further includes an insulator configured and arranged to electrically insulate each of the at least one inner cylinder and the outer cylinder.

In another embodiment, a device for brain stimulation includes a lead having a longitudinal surface and a distal end. The lead includes a plurality of cylinder assemblies disposed along the longitudinal surface of the lead body near the distal end of the lead. Each of the plurality of cylinder assemblies includes at least one inner conductive cylinder having at least one inner window and a concentric outer conductive cylinder having at least one outer window.

In yet another embodiment, a method of manufacturing a device for brain stimulation includes forming a lead body having a distal end section. At least one inner conductive cylinder is introduced about the circumference of the lead body at the distal end section, the at least one inner cylinder having at least one inner window. An outer conductive cylinder is secured around the at least one inner cylinder, the outer cylinder having at least one outer window. Each of the at least one inner cylinder and the outer cylinder is electrically insulated from each other using an insulator.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of devices and methods for brain stimulation including deep brain stimulation. In addition, the invention is directed to devices and method for brain stimulation using a lead having a plurality of concentric windowed cylinders.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. See, for instance, U.S. Patent Publication 2006/0149335 A1 ("Devices and Methods For Brain Stimulation"), and co-pending patent application Ser. No. 12/237,888 ("Leads With Non-Circular-Shaped Distal Ends For Brain Stimulation Systems and Methods of Making and Using"). Each of these references is incorporated herein by reference in its respective entirety.

Figure 12:
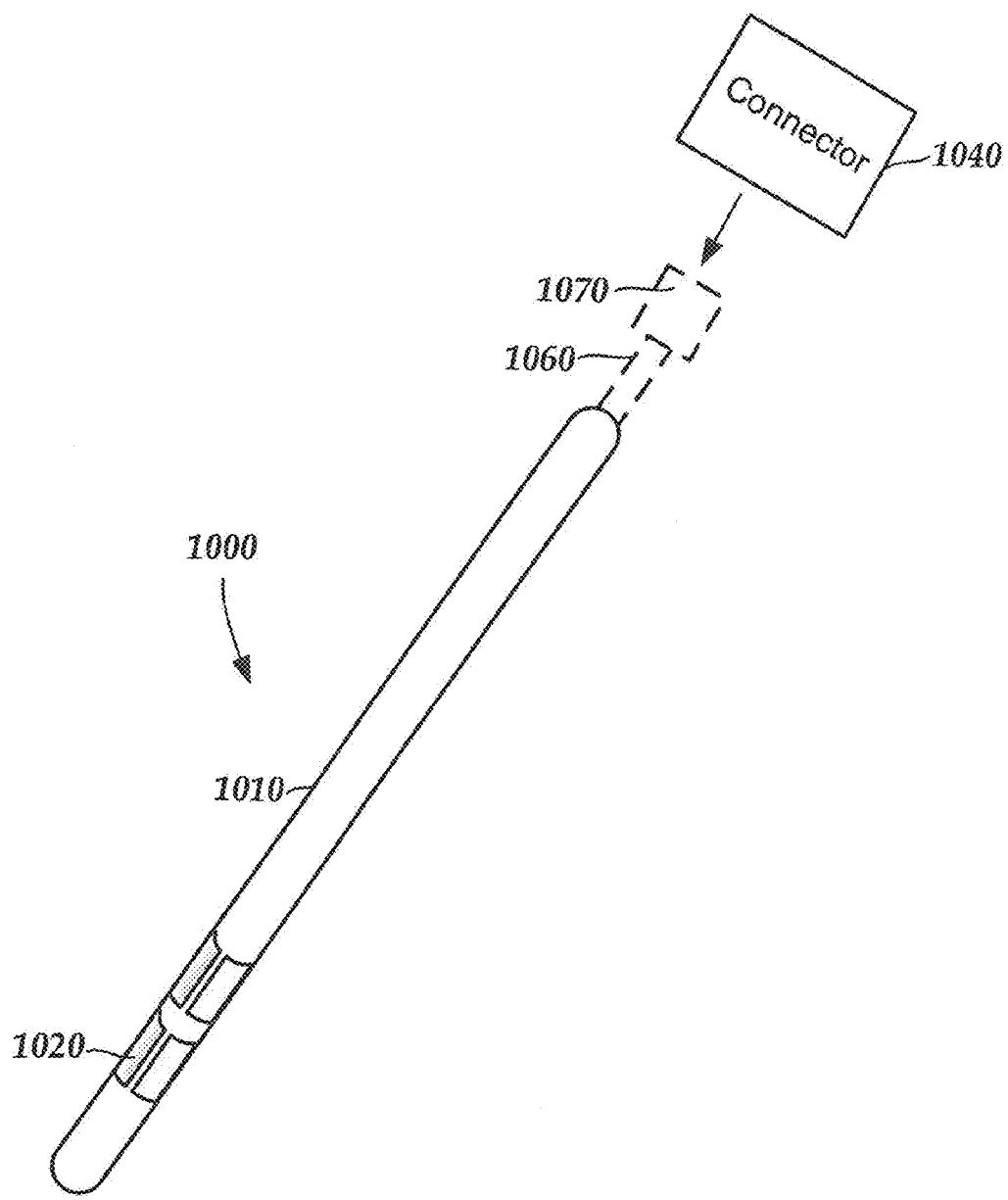
FIG. 12 is a schematic side view of one embodiment of a device for brain stimulation, according to the invention.

FIG. 12 illustrates one embodiment of a device 1000 for brain stimulation. The device includes a lead 1010, segmented electrodes 1020, a connector 1040 for connection of the electrodes to a control unit, and a stylet 1060 for assisting in insertion and positioning of the lead in the patient's brain. The stylet 1060 can be made of a rigid material. Examples of suitable materials include tungsten, stainless steel, or plastic. The stylet 1060 may have a handle 1070 to assist insertion into the lead, as well as rotation of the stylet and lead. The connector 1040 fits over the proximal end of the lead 1010, preferably after removal of the stylet 1060.

In one example of operation, access to the desired position in the brain can be accomplished by drilling a hole in the patient's skull or cranium with a cranial drill (commonly referred to as a burr), and coagulating and incising the dura mater, or brain covering. The lead 1010 can be inserted into the cranium and brain tissue with the assistance of the stylet 1060. The lead can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): rotate the lead, insert the lead, or retract the lead. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

It will be understood that the lead 1010 for deep brain stimulation can include stimulation electrodes, recording electrodes, or both. In at least some embodiments, the lead is rotatable so that the stimulation electrodes can be aligned with the target neurons after the neurons have been located using the recording electrodes.

Stimulation electrodes may be disposed on the circumference of the lead to stimulate the target neurons. Stimulation electrodes may be ring-shaped so that current projects from each electrode equally in every direction at any given length along the axis of the lead. To achieve current steering, segmented electrodes can be utilized additionally or alternatively. Though the following description discusses stimulation electrodes, it will be understood that all configurations of the stimulation electrodes discussed may be utilized in arranging recording electrodes as well.

Figure 1A:
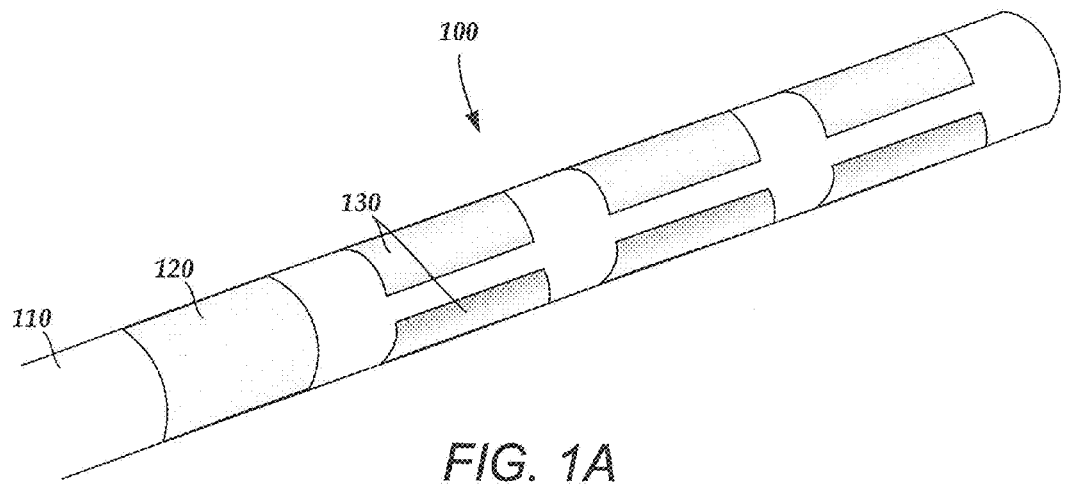
FIG. 1A is a schematic perspective view of one embodiment of a portion of a lead having a plurality of segmented electrodes and a ring electrode, according to the invention.

FIG. 1A illustrates one embodiment of a lead 100. The device includes a lead body 110, one or more ring electrodes 120, and a plurality of segmented electrodes 130. The lead body 110 can be formed of a biocompatible, non-conducting material such as, for example, a polymeric material. Suitable polymeric materials include, but are not limited to, silicone, polyethylene, polyurethanes, polyureas, or polyurethane-ureas. In at least some instances, the lead may be in contact with body tissue for extended periods of time. In at least some embodiments, the lead has a cross-sectional diameter of no more than 1.5 mm and may be in the range of 0.75 to 1.5 mm. In at least some embodiments, the lead has a length of at least 10 cm and the length of the lead may be in the range of 25 to 70 cm.

Stimulation electrodes may be disposed on the lead body 110. These stimulation electrodes may be made using a metal, alloy, conductive oxide, or any other suitable conductive material. Examples of suitable materials include, but are not limited to, platinum, iridium, platinum iridium alloy, stainless steel, titanium, or tungsten. Preferably, the stimulation electrodes are made of a material that is biocompatible and does not substantially corrode under expected operating conditions in the operating environment for the expected duration of use.

In at least some embodiments, any of the electrodes can be used as an anode or cathode and carry anodic or cathodic current. In some instances, an electrode might be an anode for a period of time and a cathode for a period of time. In other embodiments, the identity of a particular electrode or electrodes as an anode or cathode might be fixed.

The lead contains a plurality of segmented electrodes 130. Any number of segmented electrodes 130 may be disposed on the lead body 110. In some embodiments, the segmented electrodes 130 are grouped in sets of segmented electrodes, each set disposed around the circumference of the lead at or near a particular longitudinal position. The lead may have any number of sets of segmented electrodes. In at least some embodiments, the lead has one, two, three, four, five, six, seven, or eight sets of segmented electrodes. In at least some embodiments, each set of segmented electrodes contains the same number of segmented electrodes 130. In some embodiments, each set of segmented electrodes contains three segmented electrodes 130. In at least some other embodiments, each set of segmented electrodes contains two, four, five, six, seven or eight segmented electrodes. The segmented electrodes 130 may vary in size and shape. For example, in FIG. 1B, the segmented electrodes 130 are shown as portions of a ring or curved rectangular portions. In some other embodiments, the segmented electrodes 130 are curved square portions. The shape of the segmented electrodes 130 may also be substantially triangular, diamond-shaped, oval, circular or spherical. In some embodiments, the segmented electrodes 130 are all of the same size, shape, diameter, width or area or any combination thereof. In some embodiments, the segmented electrodes of each set (or even all segmented electrodes) may be identical in size and shape.

In at least some embodiments, each set of segmented electrodes 130 may be disposed around the circumference of the lead body 110 to form a substantially or approximately cylindrical shape around the lead body 110. The spacing of the segmented electrodes 130 around the circumference of the lead body 110 may vary. In at least some embodiments, equal spaces, gaps or cutouts are disposed between each segmented electrodes 130 around the circumference of the lead body 110. In other embodiments, the spaces, gaps or cutouts between segmented electrodes may differ in size or shape. In other embodiments, the spaces, gaps, or cutouts between segmented electrodes may be uniform for a particular set of segmented electrodes or for all sets of segmented electrodes. The segmented electrodes 130 may be positioned in irregular or regular intervals around the lead body 110.

Stimulation electrodes in the form of ring electrodes 120 may be disposed on any part of the lead body 110, usually near a distal end of the lead. FIG. 1A illustrates a portion of a lead having one ring electrode. Any number of ring electrodes may be disposed along the length of the lead body 110. For example, the lead body may have one ring electrode, two ring electrodes, three ring electrodes or four ring electrodes. In some embodiments, the lead will have five, six, seven or eight ring electrodes. Other embodiments do not include ring electrodes.

In some embodiments, the ring electrodes 120 are substantially cylindrical and wrap around the entire circumference of the lead body 110. In some embodiments, the outer diameter of the ring electrodes 120 is substantially equal to the outer diameter of the lead body 110. Furthermore, the width of ring electrodes 120 may vary according to the desired treatment and the location of the target neurons. In some embodiments the width of the ring electrode 120 is less than or equal to the diameter of the ring electrode 120. In other embodiments, the width of the ring electrode 120 is greater than the diameter of the ring electrode 120.

Conductors (not shown) that attach to or from the ring electrodes 120 and segmented electrodes 130 also pass through the lead body 110. These conductors may pass through the material of the lead or through a lumen defined by the lead. The conductors are presented at a connector for coupling of the electrodes to a control unit (not shown). In one embodiment, the stimulation electrodes correspond to wire conductors that extend out of the lead body 110 and are then trimmed or ground down flush with the lead surface. The conductors may be coupled to a control unit to provide stimulation signals, often in the form of pulses, to the stimulation electrodes.

Figure 1B:
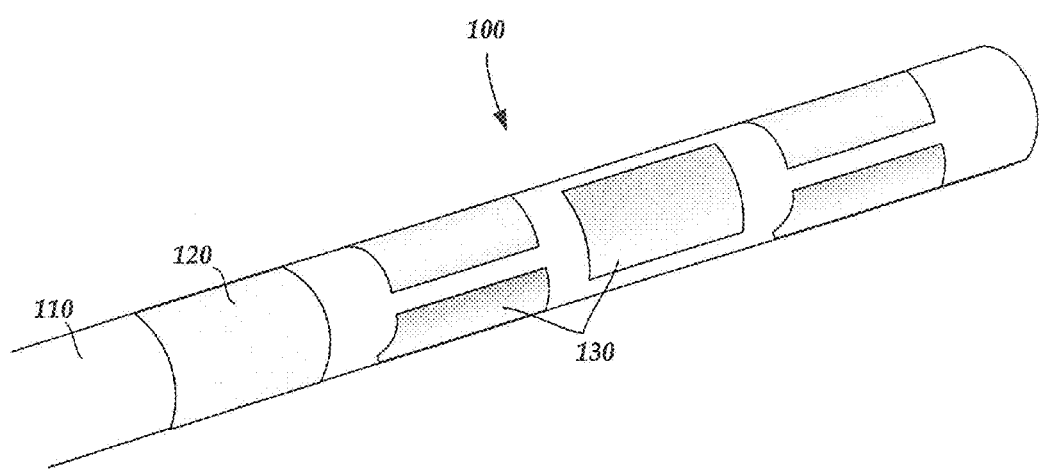
FIG. 1B is a schematic perspective view of another embodiment of a lead having a plurality of segmented electrodes arranged in staggered orientation and a ring electrode, according to the invention.

FIG. 1B is a schematic perspective view of another embodiment of a lead having a plurality of segmented electrodes. As seen in FIG. 1B, the plurality of segmented electrodes 130 may be arranged in different orientations relative to each other. In contrast to FIG. 1A, where the three sets of segmented electrodes are aligned along the length of the lead body 110, FIG. 1B displays another embodiment in which the three sets of segmented electrodes 130 are staggered. In at least some embodiments, the sets of segmented electrodes are staggered such that no segmented electrodes are aligned along the length of the lead body 110. In some embodiments, the segmented electrodes may be staggered so that at least one of the segmented electrodes is aligned with another segmented electrode of a different set, and the other segmented electrodes are not aligned.

Any number of segmented electrodes 130 may be disposed on the lead body 110 in any number of sets. FIGS. 1A and 1B illustrate embodiments including three sets of segmented electrodes. These three sets of segmented electrodes 130 may be disposed in different configurations. For example, three sets of segmented electrodes 130 may be disposed on the distal end of the lead body 110, distal to a ring electrode 120. Alternatively, three sets of segmented electrodes 130 may be disposed proximal to a ring electrode 120. By varying the location of the segmented electrodes 130, different coverage of the target neurons may be selected. For example, a specific configuration may be useful if the physician anticipates that the neural target will be closer to the distal tip of the lead body 110, while another arrangement may be useful if the physician anticipates that the neural target will be closer to the proximal end of the lead body 110. In at least some embodiments, the ring electrodes 120 alternate with sets of segmented electrodes 130.

Any combination of ring electrodes 120 and segmented electrodes 130 may be disposed on the lead. In some embodiments the segmented electrodes are arranged in sets. For example, a lead may include a first ring electrode 120, two sets of segmented electrodes, each set formed of three segmented electrodes 130, and a final ring electrode 120 at the end of the lead. This configuration may simply be referred to as a 1-3-3-1 configuration. It may be useful to refer to the electrodes with this shorthand notation. Other eight electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. In some embodiments, the lead will have 16 electrodes. Possible configurations for a 16-electrode lead include, but are not limited to 4-4-4-4, 8-8, 3-3-3-3-3-1 (and all rearrangements of this configuration), and 2-2-2-2-2-2-2-2.

Figure 2:
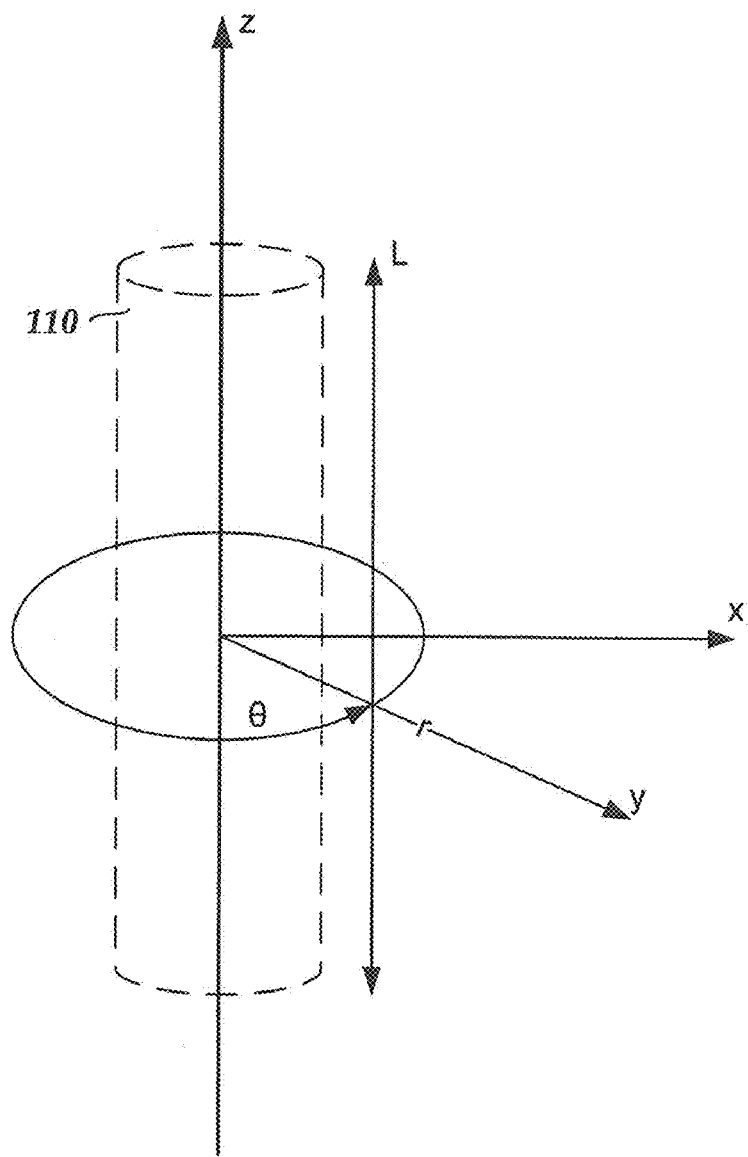
FIG. 2 is a schematic diagram of radial current steering along various electrode levels along the length of a lead, according to the invention.

FIG. 2 is a schematic diagram to illustrate radial current steering along various electrode levels along the length of a lead. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead body 110. In some embodiments, the radial distance, r, and the angle θ around the circumference of the lead body 110 may be dictated by the percentage of anodic current (recognizing that stimulation predominantly occurs near the cathode, although strong anodes may cause stimulation as well) introduced to each electrode as will be described in greater detail below. In at least some embodiments, the configuration of anodes and cathodes along the segmented electrodes 130 allows the centroid of stimulation to be shifted to a variety of different locations along the lead body 110.

As can be appreciated from FIG. 2, the centroid of stimulation can be shifted at each level along the length of the lead. The use of multiple sets of segmented electrodes 130 at different levels along the length of the lead allows for three-dimensional current steering. In some embodiments, the sets of segmented electrodes 130 are shifted collectively (i.e. the centroid of simulation is similar at each level along the length of the lead). In at least some other embodiments, each set of segmented electrodes 130 is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 130 are utilized to allow for true 360° selectivity.

In addition to 360° selectivity, a lead having segmented electrodes may provide several advantages. First, the lead may provide for more directed stimulation, as well as less "wasted" stimulation (i.e. stimulation of regions other than the target region). By directing stimulation toward the target tissue, side effects may be reduced. Furthermore, because stimulation is directed toward the target site, the battery in an implantable pulse generator may last for a longer period of time between recharging.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

Radially segmented electrode arrays may be manufactured in a variety of ways. In at least some embodiments, concentric cylindrical electrodes having windowed portions may be used to form a radially segmented electrode array. The plurality of cylindrical electrodes may be modified to utilize different numbers of electrodes, to adjust the radial spacing between electrodes or to vary the longitudinal position between levels of electrodes.

Figure 3B:
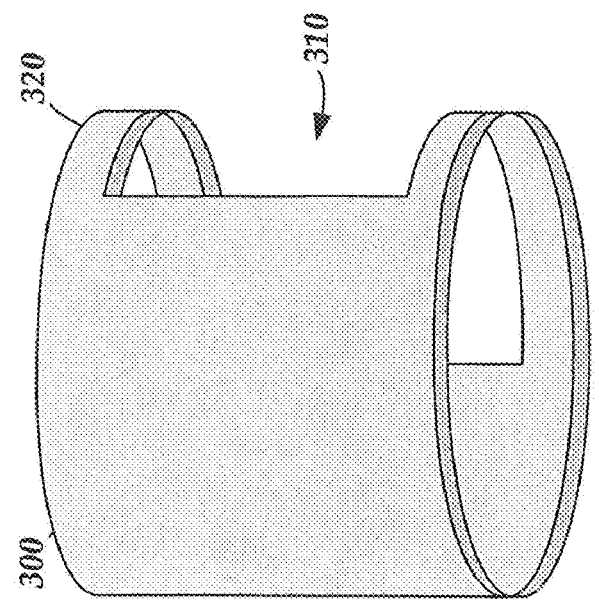
FIG. 3B is a schematic perspective view of the inner cylinder of FIG. 3A after formation of a window, according to the invention.
Figure 3A:
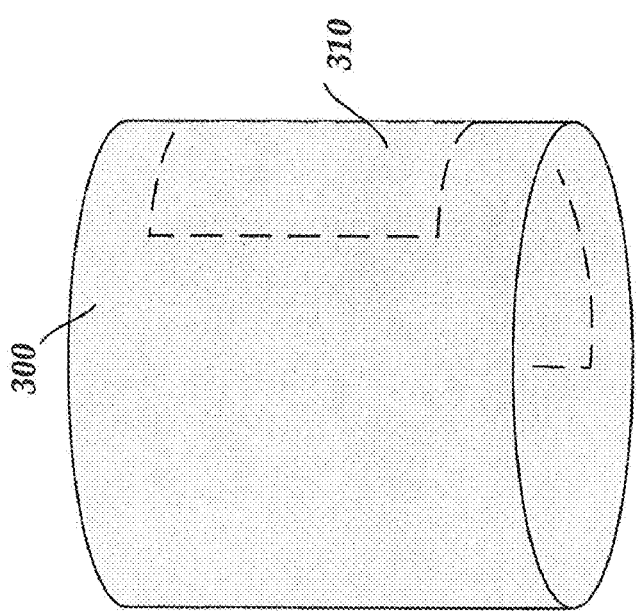
FIG. 3A is a schematic perspective view of one embodiment of an inner cylinder, according to the invention.

FIG. 3A is a schematic perspective view of one embodiment of an inner cylinder 300. As will be explained further below, the shape and size of the inner cylinder 300 may be modified. Furthermore, the inner cylinder 300 may be formed from a metal, alloy, conductive oxide, or any other suitable conductive material. In some embodiments, the inner cylinder 300 is formed of platinum, platinum-iridium, iridium, 316L stainless steel, tantalum, nitinol or a conductive polymer. As seen in FIG. 3A, the inner cylinder 300 may include an inner window 310. The size and shape of the inner window 310 of the inner cylinder 300 may also be modified.

The inner cylinder 300 may also include an inner window 310. FIG. 3A illustrates one embodiment of an inner window 310 that is cut from the inner cylinder 300. As seen in FIG. 3A, the inner window 310 of the inner cylinder 310 may be formed of a rectangular section that is cut from the inner cylinder 310 about the circumference. It will be understood that the size and shape of the inner window 310 may vary. For example, in some embodiments, the inner window 310 may be formed in the shape of a square. Alternatively, the inner window 310 may be formed such that the width about the circumference of the inner cylinder 300 is longer or shorter than the length of the inner window 310. The inner window 310 may also be formed of different shapes. For example, the inner window 310 may be formed of a square, a triangle, a circle or a diamond.

The inner cylinder 300 may also include more than one inner window 310. For example, in some embodiments, two inner windows 310 may be formed in the inner cylinder 300. It will be understood that any number of inner windows 310 may be formed in the inner cylinder 300 (e.g. two, there, four, five, six, seven, eight, ten or twelve windows.) These inner windows 310 may be disposed at regular intervals about the circumference of the inner cylinder 300. In some embodiments, each of the inner windows 310 of the inner cylinder 300 is formed in a different shape. Alternatively, in some embodiments, the inner windows 310 are formed of the same shape and size.

FIG. 3B is a schematic perspective view of the inner cylinder 300 of FIG. 3A after formation of an inner window 310. The inner window 310 may be formed in the inner cylinder 300 through any suitable method. For example, an inner window 310 may be laser cut through the inner cylinder 300. As seen in FIG. 3B, the resulting structure is an inner cylinder 300 having an inner window 310 that extends along half the circumference of the inner cylinder 300. Furthermore, the inner window 310 may be cut so that ring portions 320 remain along the top and bottom of the cylinder. The ring portions 320 may be useful in coupling the inner cylinder 300 onto the lead 100. It will be understood that the ring portions 320 may be of any suitable size or thickness, depending on the desired size of the inner window 310.

Figure 4B:
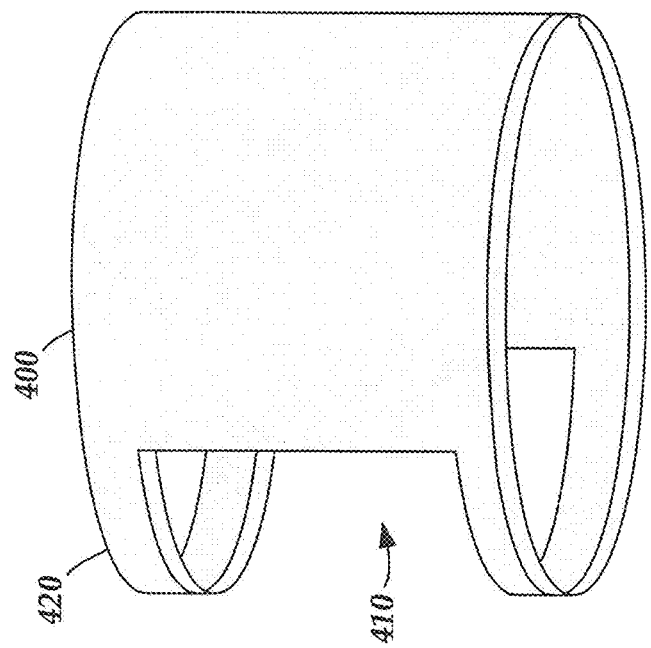
FIG. 4B is a schematic perspective view of the outer cylinder of FIG. 4A after formation of a window, according to the invention.
Figure 4A:
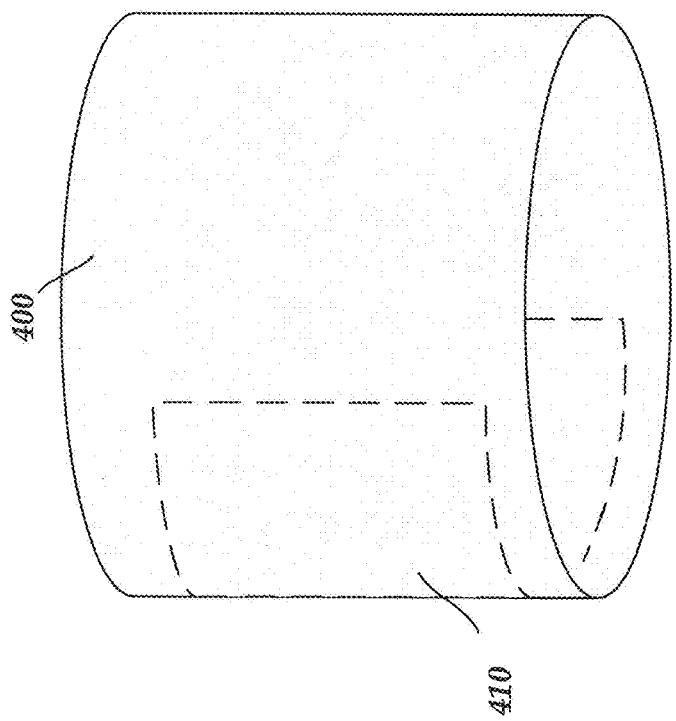
FIG. 4A is a schematic perspective view of one embodiment of an outer cylinder, according to the invention.

FIG. 4A is a schematic perspective view of one embodiment of an outer cylinder 400. The outer cylinder 400 may be formed of any suitable conductive material, such as those described above with respect to the inner cylinder 300. In some embodiments, the outer cylinder 400 and the inner cylinder 300 are formed of the same conductive material. In at least some other embodiments, the outer cylinder 400 and the inner cylinder 300 are formed of different conductive materials.

The outer cylinder 400 may also be formed in different shapes and sizes. For example, the length of the outer cylinder 400 may be increased or decreased as desired. In at least some embodiments, the length of the outer cylinder 400 is the same as the length of the inner cylinder 300. Alternatively, the outer cylinder 400 may be shorter or longer than the inner cylinder 300. The diameter of the outer cylinder 400 may also be modified. For example, the inner diameter of the outer cylinder 400 may correspond to the outer diameter of the inner cylinder 300. In some embodiments, the inner diameter of the outer cylinder 400 is slightly larger than the outer diameter of the inner cylinder 300. It may be desirable to form an isodiametric lead. In some embodiments, the outer diameter of the outer cylinder 400 corresponds to the diameter of the lead body.

The outer cylinder 400 may also include an outer window 410. The outer window 410 may be formed in an suitable shape and size as described with reference to the inner window 310 of the inner cylinder 300. In some embodiments, the outer window 410 is formed in the same shape as that of the inner window 310. In some embodiments, the outer window 410 is formed in a shape that is complementary to the shape of the uncut portion of the inner cylinder 300. The outer cylinder 400 may also include more than one outer window 410. For example, in some embodiments, two, three, four, five, six, seven, eight, ten or twelve outer windows 410 may be formed in the outer cylinder 400. The number of outer windows 410 formed may correspond to the number of uncut portions remaining on the inner cylinder 300 after the inner windows 310 have been formed.

The outer windows 410 may be cut so that ring portions 420 remain along the top and bottom of the outer cylinder 400. The ring portions 420 may be useful in coupling the outer cylinder 400 to the inner cylinder 300 and the lead body 110. It will be understood that the ring portions 420 may be of any suitable size or thickness, depending on the desired size of the outer window 410. In some embodiments, the ring portions 420 are of the same shape and size as those of the inner cylinder 300. The ring portions 420 and the outer window 410 may be formed by laser cutting a portion of the outer cylinder 400 as described above. FIG. 4B is a schematic perspective view of the outer cylinder of FIG. 4A after formation of a window.

In some embodiments, the inner cylinder 300 and the outer cylinder 400 may be coupled to one another to form a cylinder assembly. For example, the inner cylinder 300 may be disposed within the outer cylinder 400. In some embodiments, the inner cylinder 300 is slid into the outer cylinder 400 and the two are secured using any suitable methods. The manufacture, arrangement and configuration of the cylinder assembly will be more thoroughly discussed with reference to FIGS. 5-7.

Figure 5:
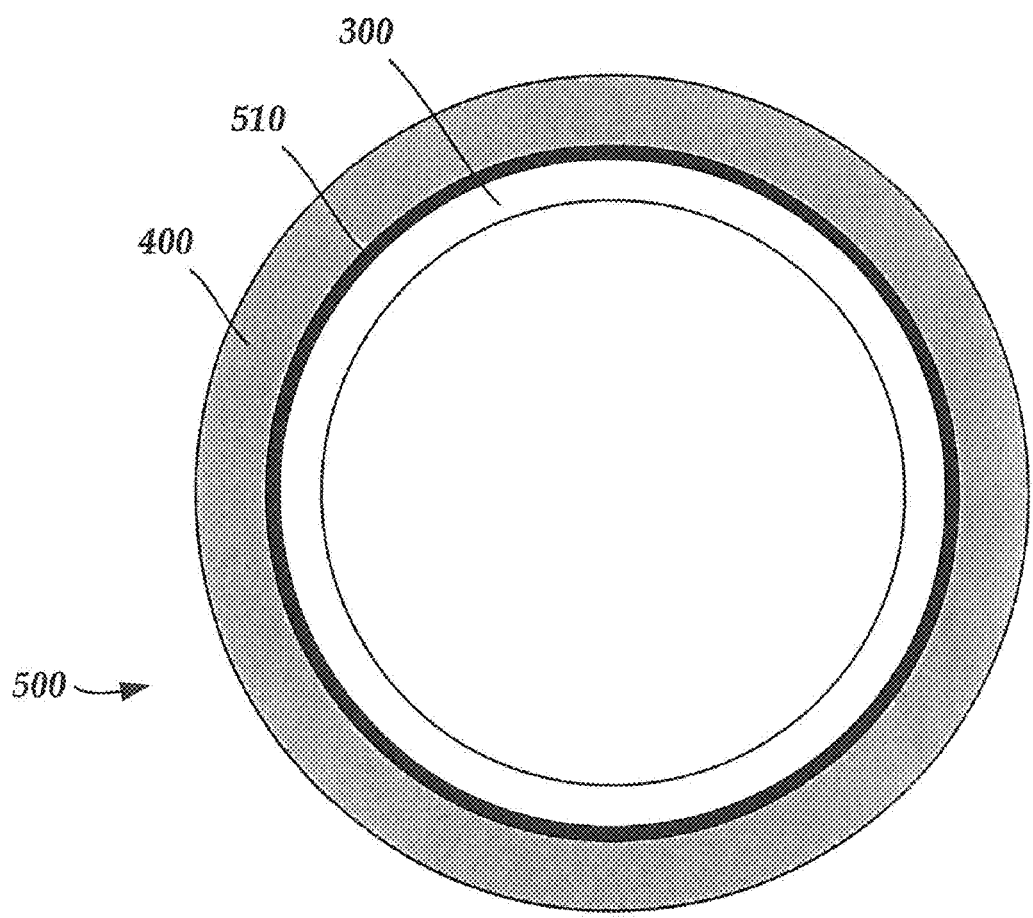
FIG. 5 is a schematic cross-sectional view of one embodiment of a cylinder assembly having an inner cylinder, an outer cylinder and an insulator, according to the invention.

FIG. 5 is a schematic cross-sectional view of one embodiment of a cylinder assembly 500 having an inner cylinder 300, an outer cylinder 400 and an insulator 510. As seen in FIG. 5, the inner diameter of the outer cylinder 400 is slightly larger than the outer diameter of the inner cylinder 300. Furthermore, an insulator 510 may be applied to the inner cylinder 300, the outer cylinder 400 or both, to electrically insulate them from one another.

The insulator 510 may include any suitable insulator such as, for example, silicone, suitable fluoropolymers, polyurethane, PEEK, polysulfone, nylon, Teflon®, thermoplastics, other liquid crystal polymers or some other implant grade non-conductive material. It will be understood that the insulators listed above are given by way of example and that any suitable insulator may be used. In some embodiments, the insulator 510 includes a thin cylinder of insulative material. Furthermore, the insulator 510 may be formed of any combination of the materials described above. In the case of silicone and certain other insulators, the insulator 510 may be applied using a dip coating technique. The insulator 510 may be useful may be useful in electrically separating two adjacent cylinders.

In some embodiments, the insulator 510 covers the entirety or a substantial portion of the outer diameter of the inner cylinder 300. Additionally, the insulator 510 may be applied to the inner diameter of the outer cylinder 400. Thus, the insulator 510 may applied to either of the cylinders. In at least some other embodiments, the insulator 510 is applied to both the inner cylinder 300 and the outer cylinder 400. Thus, by using an insulator 510, a cylinder assembly may be formed having two portions, each portion corresponding to one of the cylinders and being configured to function independently of the other.

Figure 6:
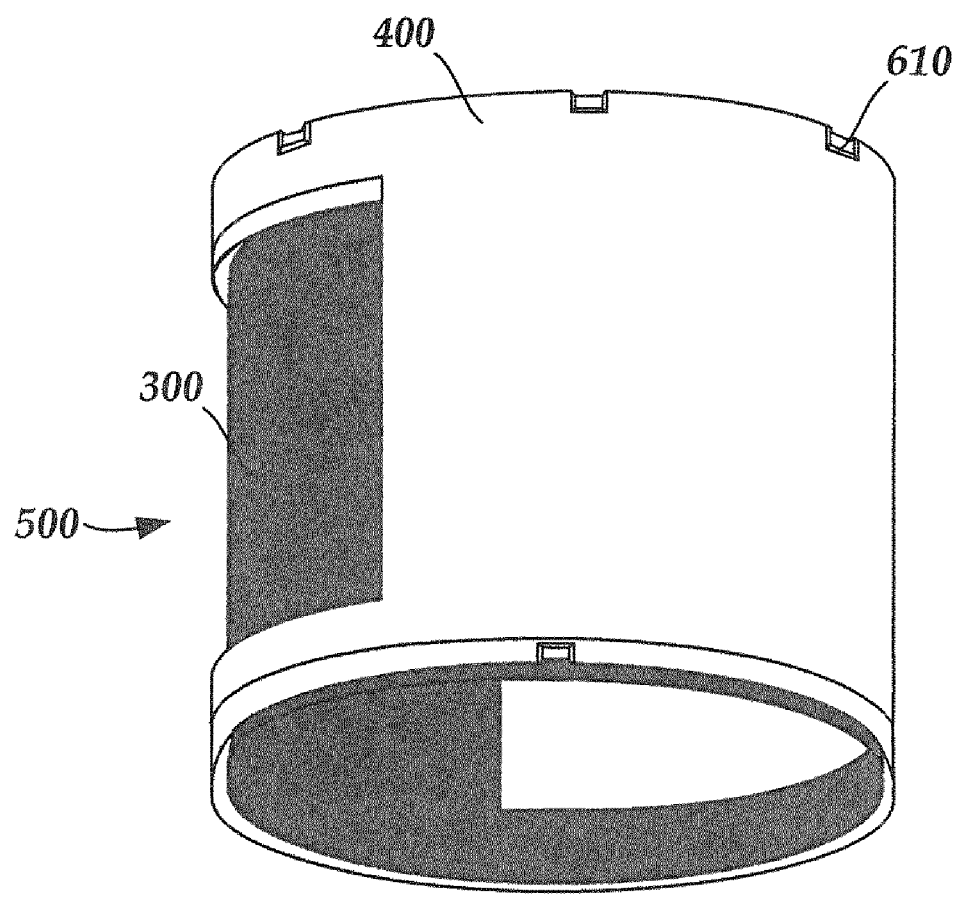
FIG. 6 is a schematic perspective view of an inner cylinder disposed within the outer cylinder, according to the invention.

FIG. 6 is a schematic perspective view of an inner cylinder 300 disposed within the outer cylinder 400. As seen in FIG. 6, the inner cylinder 300 may be fully housed within the outer cylinder 400. In some embodiments, the inner cylinder 300 and the outer cylinder 400 are concentric. The inner cylinder 300 and the outer cylinder 400 may also be arranged such that the cylinders are aligned longitudinally. Furthermore, the inner window 310 and the outer window 410 may be aligned in a variety of arrangements. In some embodiments, the inner cylinder 300 and the outer cylinder 400 are aligned such that a portion of the inner cylinder 300 is exposed through the outer window 410 of the outer cylinder 400.

The inner cylinder 300 and the outer cylinder 400 may be coupled together using a variety of methods. For example, in some embodiments, the outer cylinder 400 is crimped down on the inner cylinder 300 at various locations to create a mechanical connection between the two cylinders. The crimped portions 610 may be disposed around the circumference of the ring portions 320 and 420. In some embodiments, the crimped portions 610 are disposed at one end of the two cylinders. As shown in FIG. 6, the crimped portions 610 may also be disposed at both ends at various intervals along the circumference of the ring portions. In at least some other embodiments, a swaging process is used to secure the inner cylinder 300 to the outer cylinder 400. It will be understood that any method of securing the two cylinders can be used to create the cylinder assembly. For example, instead of mechanically deforming the two cylinders, a suitable biocompatible adhesive may be used to couple the two cylinders.

An insulator 510 may be applied to the cylinder assembly 500. The insulator 510 may be any one of or a combination of the insulators disposed between the inner cylinder 300 and the outer cylinder 400. In some embodiments, the entire cylinder assembly 500 is coated with an insulator 510 and portions of the insulator 510 are removed from areas that will be used as electrodes. For example, if circular electrodes are desired, an insulator 510 may be used to cover the entire cylinder assembly 500 and a circular portion of the insulator 510 may be removed from the outside surface of the outer cylinder. Any method of removing the undesired insulator 510 may be used. In some embodiments, laser ablation is used to remove the insulator 510 from the surface of the cylinders in the shape of the desired electrodes.

Figure 7:
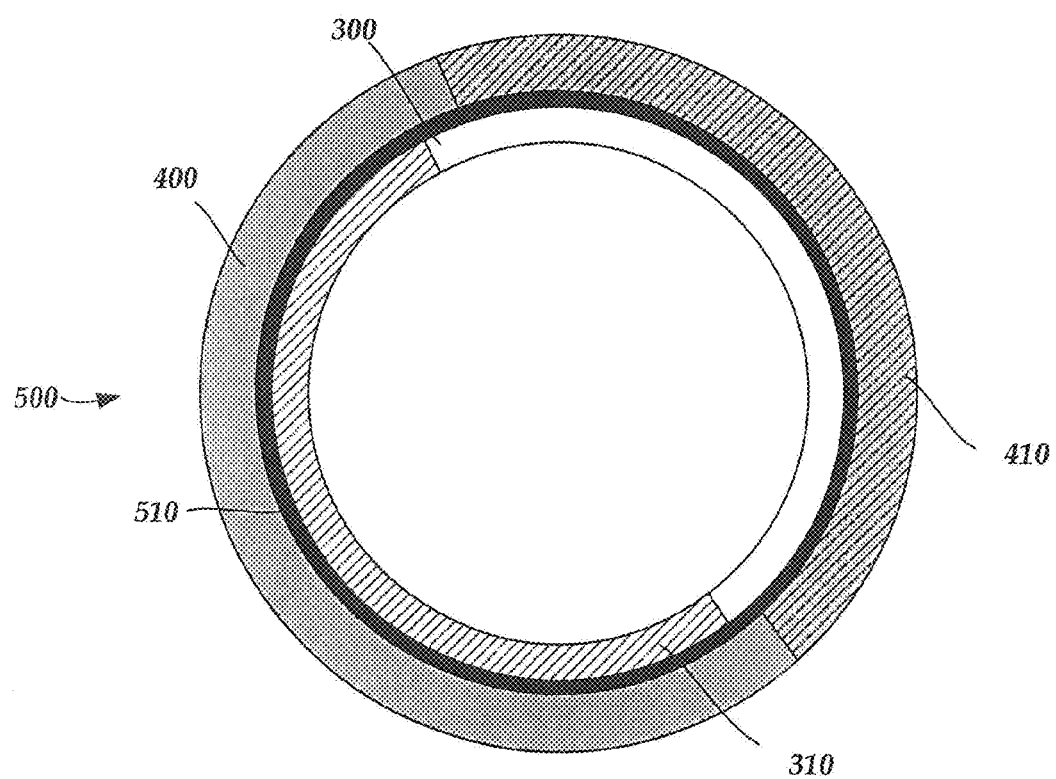
FIG. 7 is a schematic cross-sectional view of one embodiment of a cylinder assembly showing the location of the inner window and the outer window, according to the invention.

FIG. 7 is a schematic cross-sectional view of one embodiment of a cylinder assembly 500 showing the location of the inner window and the outer window. It will be understood that the inner cylinder 300 may be rotated within the outer cylinder 400 in a plurality of arrangements prior to coupling the two. Thus, in some embodiments, the outer window 410 is aligned with an uncut portion of the inner cylinder 300 so that the inner cylinder 300 is capable of stimulating tissue through the outer window 400. In embodiments where the cylinders are used as recording electrodes, the inner cylinder 300 may likewise be aligned with the outer windows 410 to achieve proper measurement of an electrical signal. The inner window 310 of the inner cylinder 300 and the outer window 410 of the outer cylinder 400 may be aligned such that no portions of the cylinders overlap except for the ring portions 320 and 420. Thus, the inner window 310 may be completely aligned with the uncut portion of the outer cylinder 400 and the outer window 410 may be completely aligned with the uncut portion of the inner cylinder 300. It will be understood that in at least some other embodiments, the uncut portions of the inner cylinder 300 and outer cylinder 400 at least partially overlap.

Furthermore, in embodiments having multiple inner windows 310 and/or multiple outer windows 410, a combination of overlapping and non-overlapping portions may be formed with two cylinders.

Figure 8:
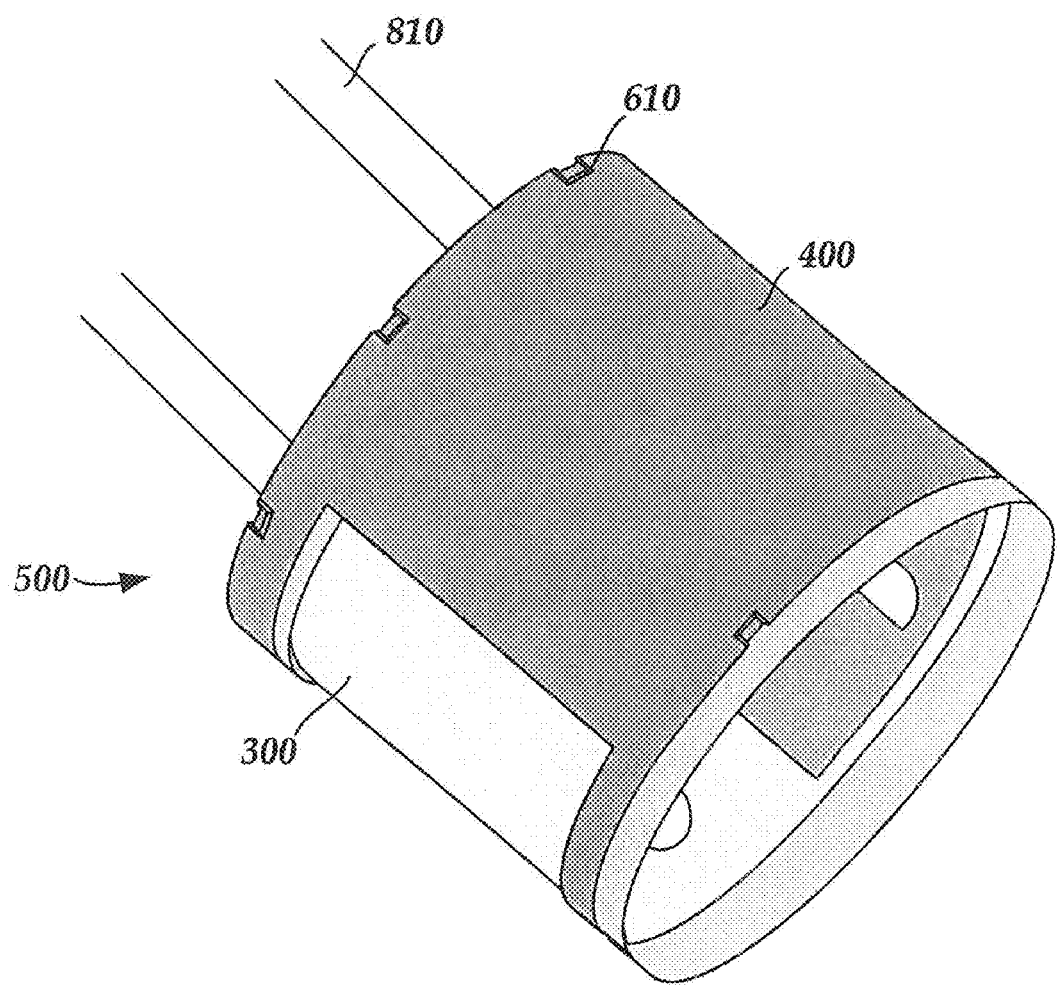
FIG. 8 is a schematic perspective view of a cylinder assembly coupled to a plurality of conductors, according to the invention.

Conductors 810 may be attached to any portion of the inner cylinder 310 and/or outer cylinder 410. For example, conductors may be attached to the uncut portions of the cylinders or to the ring portions of the cylinders. FIG. 8 is a schematic perspective view of a cylinder assembly 500 coupled to a plurality of conductors 810. The outer cylinder 400 is crimped down onto the inner cylinder 300 at crimped portions 610. As seen in FIG. 8, the conductors may extend through and disposed inside the two cylinders. Thus, in some embodiments, a piece of the insulator 510 may be removed so that that conductor 810 can properly attach to one of the cylinders. Any method of removing a fragment of the insulator 510 may be used. In some embodiments, an ablation process is used to remove pieces of the insulator 510 so that conductors 810 may be attached to the cylinders. In some embodiments, the conductors 810 are laser welded to the inner cylinder 300 and outer cylinder 400.

Any number of conductors 810 may be coupled to the cylinders. In some embodiments, each cylinder is coupled to a designated conductor 810. In at least some other embodiments, multiple conductors 810 are coupled to each of the cylinders. The same or a different number of conductors 810 may be coupled to each of the cylinders. Thus, in this manner the cylinder assembly 500 may be formed to have two or more independent electrodes composed of the inner and outer cylinders.

It will be understood that as explained, in some embodiments, the outer cylinder 400 forms one set of one or more electrodes and the inner cylinder 300 forms another set of electrodes. The set of electrodes disposed on the inner cylinder 300 may be recessed because of their radial positioning with respect to the outer cylinder 400.

Figure 9:
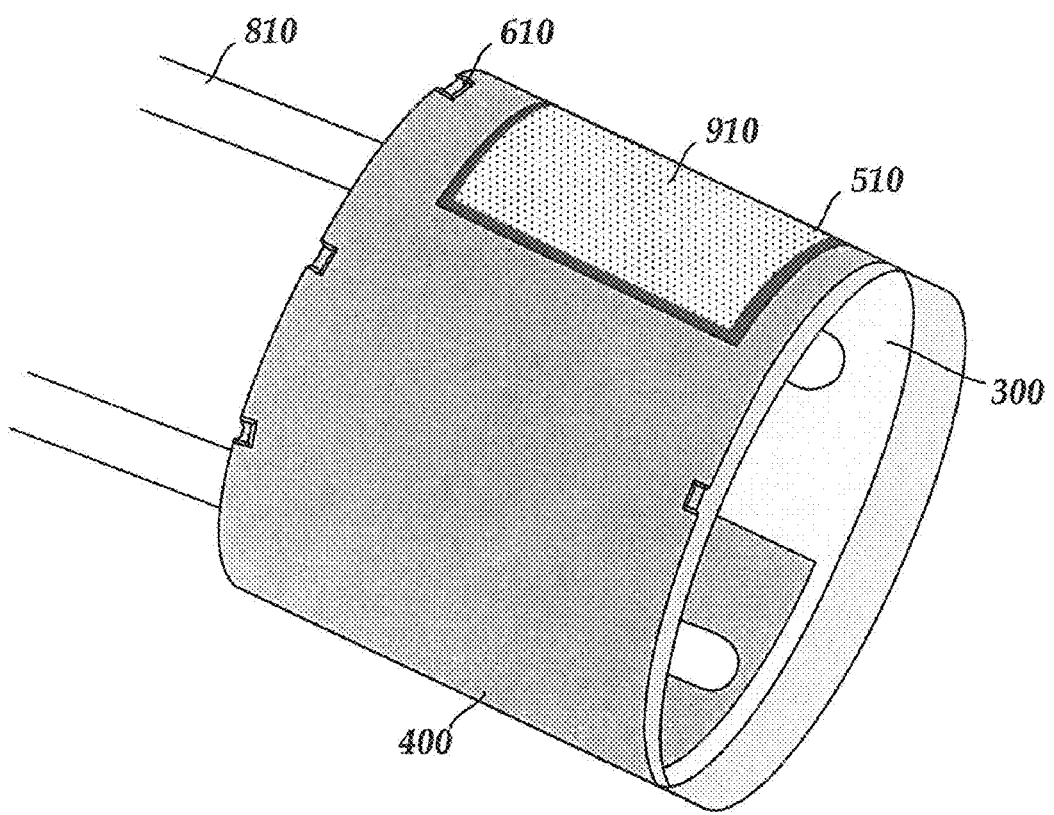
FIG. 9 is a schematic perspective view of a cylinder assembly having an elevating plate and coupled to a plurality of conductors, according to the invention.

In some embodiments, it may be desirable to create a lead 100 that is isodiametric. An elevating plate 910 disposed on a portion of the inner cylinder within the outer window 410 of the outer cylinder 400 may be used to form such a lead. FIG. 9 is a schematic perspective view of a cylinder assembly 500 having an elevating plate 910, the cylinder assembly 500 being coupled to a plurality of conductors 810. Though FIG. 9 illustrates an elevating plate 910 in the shape of a curved member, it will be understood that a variety of shapes and sizes may be used to form the elevating plate 910. In some embodiments, the shape of the elevating plate 910 corresponds to the outer window 410 of the outer cylinder 400.

As seen in FIG. 9, the elevating plate 910 may be electrically coupled to the inner cylinder 300. In some embodiments, conductors 810 are directly coupled to the elevating plate 910. The elevating plate 910 may be adhered or welded to the inner cylinder 300 through any suitable method. In some embodiments, the elevating plate 910 is unitarily formed with the inner cylinder 300 so that the inner cylinder 300 comprises a raised portion that will fit within the outer window 410 of the outer cylinder 400. In order to electrically insulate the elevating plate 910 from the outer cylinder 400, the sides of the elevating plate 910 may be coated with an insulator 510. In some embodiments, the entire elevating plate 910 is coated with an insulator 510 and portions of the insulator 510 are removed as desired (e.g. to couple the elevating plate 910 to conductors or to create electrodes in a desired shape as described above).

Figure 10A:
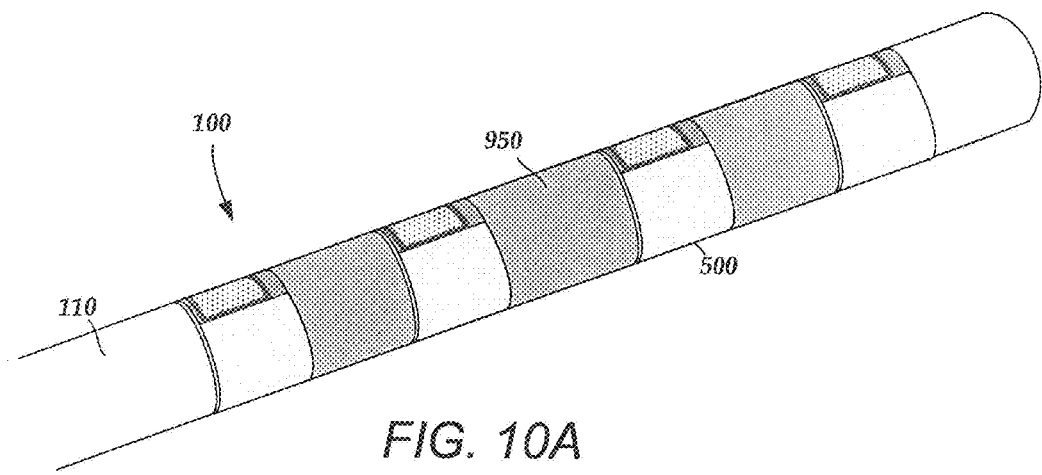
FIG. 10A is a schematic perspective view of one embodiment of a portion of a lead having a plurality of cylinder assemblies and spacers, according to the invention.

FIG. 10A is a schematic perspective view of one embodiment of a portion of a lead having a plurality of cylinder assemblies 500 and spacers 950. As seen in FIG. 10A, spacers 950 may be used to control the distance between the cylinder assemblies 500 and to electrically insulate one cylinder assembly 500 from another. Each spacer 950 may be in the form of a short cylinder or ring that separates the two cylinder assemblies 500 as illustrated in FIG. 10A. The spacers 950 may be formed of any suitable non-conductive material capable of electrically insulating the stimulating portions of the cylinder assemblies 500. It will be understood that the size and shape of the spacers 950 may be varied to separate the cylinder assemblies 500 as desired. For example, in some embodiments, the spacers 950 have the same longitudinal length as the cylinder assemblies 500. Alternatively, the spacers 950 may be shorter or longer in the longitudinal direction than the cylinder assemblies 500. The spacers 950 may also have the same outer diameter as the cylinder assemblies 500 in order to produce an isodiametric lead.

Figure 10B:
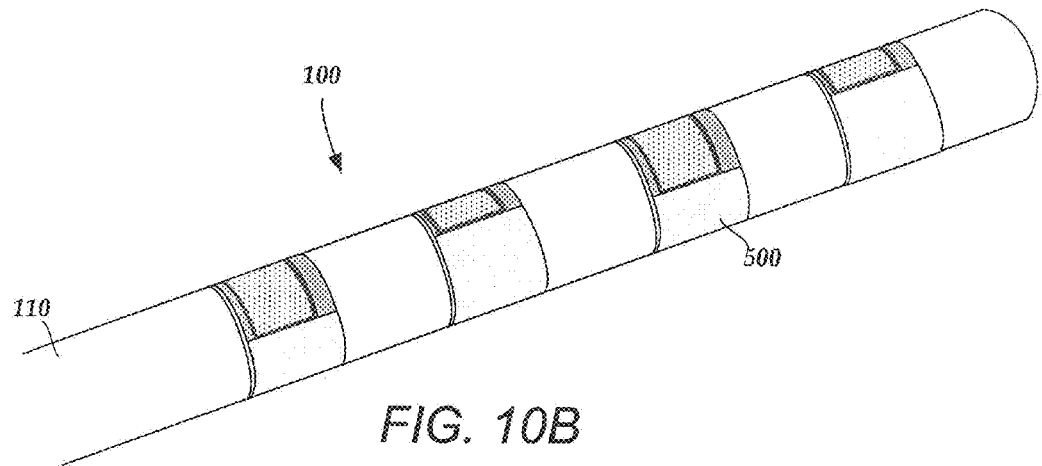
FIG. 10B is a schematic perspective view of another embodiment of a portion of a lead having a plurality of cylinder assemblies arranged in a staggered orientation, according to the invention.
Figure 11:
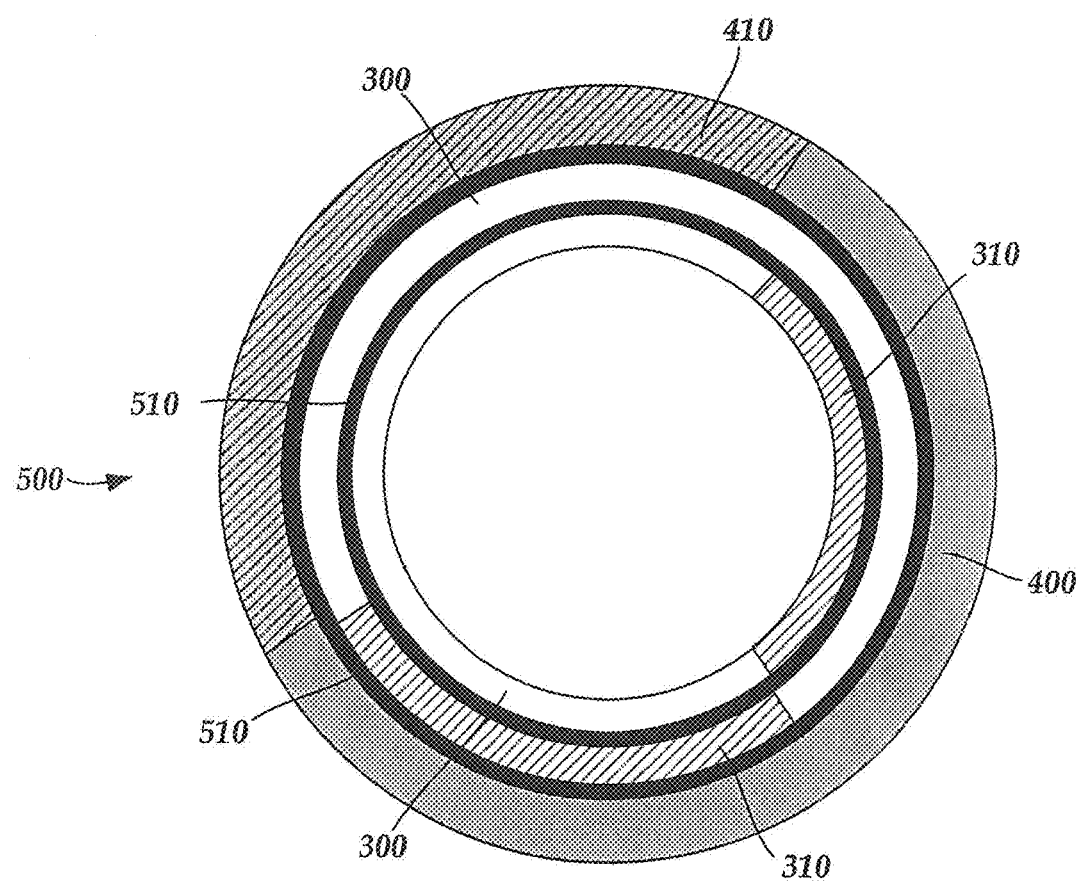
FIG. 11 is a schematic cross-sectional view of one embodiment of a cylinder assembly having two inner cylinders and one outer cylinder, according to the invention.

One of ordinary skill in the art will readily appreciate that a staggered lead arrangement may be formed using the cylinder assemblies 500 described above. FIG. 10B is a schematic perspective view of another embodiment of a portion of a lead having a plurality of cylinder assemblies 500 arranged in a staggered orientation. As seen in FIG. 10B, by rotating the cylinder assemblies 500 about the circumference of the lead body 110, a staggered lead arrangement may be formed. In some embodiments, the cylinder assemblies 500 are arranged such that successive cylinder assemblies 500 are staggered by 30, 45, 60, 90 or 120 degrees.

Modifications of these methods are possible. In some embodiments, multiple inner cylinders 300 may be disposed within the outer cylinder 400. For example, as seen in FIG. 12, a cylinder assembly 500 may be formed of a first inner cylinder 300 housed within a second inner cylinder 300, both of which are housed within an outer cylinder 400. The three cylinders may be concentric. Furthermore, windows may be formed in each of the cylinders and aligned as desired. Thus, using this technique, a cylinder assembly 500 may be formed having two, three, four, five, six, seven, eight, ten or twelve cylinders, each being insulated from the others using an insulator 510 such that each cylinder is able to stimulate the surrounding tissue with an independent set of parameters. For example, the frequency of stimulation of the first cylinder may be different than that of the second and third cylinders. Multiple conductors 810 may be disposed within the cylinders, each cylinder being coupled to a designated conductor 810. Furthermore, multiple elevating plates 910 may be used to form an isodiametric lead. Thus, by varying the number, size and shape of inner cylinders 300, it may be possible to produce leads having different stimulation and recording advantages. In some embodiments, these methods are used with lead constructions other than deep brain stimulation leads.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A device for brain stimulation, comprising:
a lead body having a distal end section;
at least one inner conductive cylinder with at least one inner window cut out from the inner cylinder, the inner cylinder disposed at the distal end section of the lead body;
an outer conductive cylinder with at least one outer window cut out from the outer cylinder, the outer cylinder being secured to and disposed concentric to the inner cylinder with a portion of each of the at least one inner cylinder aligned with the at least one outer window of the outer cylinder; and an insulator configured and arranged to electrically insulate each of the at least one inner cylinder and the outer cylinder.

2. The device of claim 1, wherein a one of the at least one inner cylinder and the outer cylinder are crimped together.

3. The device of claim 1, wherein a one of the at least one inner cylinder and the outer cylinder are swaged.

4. The device of claim 1, wherein the at least one inner window of the at least one inner cylinder is disposed at a first side of the lead body and the outer window of the outer cylinder is disposed at a second side of the lead body, the first side and second side being different.

5. The device of claim 4, wherein the first side of the lead body and the second side of the lead body are opposite sides of the lead body.

6. The device of claim 4, wherein the at least one inner window and the at least one outer window do not overlap.

7. The device of claim 1, wherein the at least one outer window of the outer cylinder is configured and arranged to allow stimulation by the at least one inner cylinder.

8. The device of claim 1, further comprising at least one conductive elevating member disposed within the outer window and coupled to a one of the at least one inner cylinder, the elevating member being arranged as isodiametric with the outer cylinder.

9. The device of claim 1, further comprising a plurality of conductors, a first one of the plurality of conductors being coupled to a one of the at least one inner cylinder, and a second one of the plurality of conductors being coupled to the outer cylinder.

10. The device of claim 9, wherein the plurality of conductors extend along the length of the lead body and are disposed inside the at least one inner cylinder.

11. The device of claim 1, wherein the insulator is disposed on the outer longitudinal surface of the at least one inner cylinder.

12. The device of claim 1, wherein the at least one inner cylinder comprises two concentric inner cylinders.

13. A device for brain stimulation, comprising:

a lead having a longitudinal surface and a distal end, the lead comprising:

a plurality of cylinder assemblies disposed along the longitudinal surface of the lead body near the distal end of the lead, each of the plurality of cylinder assemblies comprising at least one inner conductive cylinder having at least one inner window and a concentric outer conductive cylinder having at least one outer window.

14. The device of claim 13, wherein the plurality of cylinder assemblies are disposed at spaced-apart longitudinal levels along the length of the lead.

15. The device of claim 13, further comprising a spacer disposed between two of the plurality of cylinder assemblies.

16. An implantable stimulation device, comprising:
the device of claim 1; and
a control module coupleable to the lead.

17. The implantable stimulation device of claim 16, wherein the implantable stimulation device is a deep brain stimulator.

18. A method of manufacturing a device for brain stimulation, the method comprising:
i) forming a lead body having a distal end section;
ii) introducing at least one inner conductive cylinder about the circumference of the lead body at the distal end section, the at least one inner cylinder having at least one inner window;
iii) securing an outer conductive cylinder around the at least one inner cylinder, the outer cylinder having at least one outer window; and
iv) electrically insulating each of the at least one inner cylinder and the outer cylinder from each other using an insulator.

19. The method of claim 18, further comprising repeating steps ii)-iv) to form a plurality of cylinder assemblies, each cylinder assembly comprising at least one inner cylinder and an outer cylinder, the plurality of cylinder assemblies disposed at spaced-apart levels along the length of the lead body near the distal end of the lead body.

20. The method of claim 19, further comprising introducing at least one spacer at a longitudinal level along the length of the lead body, each spacer being configured and arranged to separate two of the plurality of cylinder assemblies.

* * * * *